US008883734B2

(12) United States Patent
Dal Farra et al.

(10) Patent No.: US 8,883,734 B2
(45) Date of Patent: Nov. 11, 2014

(54) PROTEASOME-ACTIVATING ANTI-AGING PEPTIDES AND COMPOSITIONS CONTAINING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 223 days.

(21) Appl. No.: 13/262,481

(22) PCT Filed: Apr. 1, 2010

(86) PCT No.: PCT/FR2010/000279
§ 371 (c)(1),
(2), (4) Date: Sep. 30, 2011

(87) PCT Pub. No.: WO2010/112712
PCT Pub. Date: Oct. 7, 2010

(65) Prior Publication Data
US 2012/0027703 A1  Feb. 2, 2012

(30) Foreign Application Priority Data
Apr. 2, 2009 (FR) ..................................... 09 01612

(51) Int. Cl.
| | |
|---|---|
| *A61K 38/06* | (2006.01) |
| *A61K 38/07* | (2006.01) |
| *A61K 38/08* | (2006.01) |
| *A61P 17/16* | (2006.01) |
| *A61Q 17/00* | (2006.01) |
| *A61Q 19/08* | (2006.01) |
| *C07K 5/103* | (2006.01) |
| *C07K 7/06* | (2006.01) |
| *A61K 8/64* | (2006.01) |
| *A61K 38/00* | (2006.01) |

(52) U.S. Cl.
CPC ................. *C07K 5/101* (2013.01); *C07K 5/109* (2013.01); *A61K 2800/522* (2013.01); *A61K 38/00* (2013.01); *A61Q 19/08* (2013.01); *C07K 7/06* (2013.01); *A61K 8/64* (2013.01)
USPC ........... 514/18.8; 514/21.8; 514/21.9; 424/59

(58) Field of Classification Search
None
See application file for complete search history.

(56) References Cited

U.S. PATENT DOCUMENTS

| | | |
|---|---|---|
| 7,220,417 B2 | 5/2007 | Nizard et al. |
| 2005/0214890 A1* | 9/2005 | Tan et al. ........................ 435/23 |
| 2008/0076718 A1 | 3/2008 | Reboud-Ravaux et al. |

FOREIGN PATENT DOCUMENTS

| | | |
|---|---|---|
| FR | 2822701 | 10/2002 |
| WO | 2005/061530 | 7/2005 |
| WO | 2006/105811 | 10/2006 |
| WO | 2007/131774 | 11/2007 |
| WO | WO 2007143006 A2 * | 12/2007 |

OTHER PUBLICATIONS

Rehemtulla et al., "The third Trp-Lys-Ser (WKS) tripeptide motif in Tissue Factor is associated with a function site", Biochem. J., 1992, pp. 737-740.*
Kivirikko et al., "Studies on Protocollagen Lysine Hydroxylase. Hydroxylation of Synthetic Peptides and the Stoichiometric Decarboxylation of a-Ketoglutarate", Biochemistry, 1972, pp. 122-129.*
PCT, International Search Report, International Application No. PCT/FR2010/000279 (mailed Sep. 22, 2010; published Nov. 25, 2010).
Petropoulos, I. et al., "Increase of Oxidatively Modified Protein Is Associated With a Decrease of Proteasome Activity and Content in Aging Epidermal Cells," *Journal of Gerontol. A. Biological Sciences*, vol. 55A, pp. B220-B227 (2000).
Kullmann, W., "Proteases as Catalysts for Enzymic Synthesis of Opioid Peptides," *The Journal of Biological Chemistry*, vol. 255, No. 17, pp. 8234-8238 (Sep. 10, 1980).
Harman, D., "Aging: A Theory Based on Free Radical and Radiation Chemistry," *Aging: Free Radical Theory*, pp. 298-300 (1992).
Glickman, M.H. et al., "The Ubiquitin-Proteasome Proteolytic Pathway: Destruction for the Sake of Construction," *Physiol. Rev.*, vol. 82, pp. 373-428 (2002).
Glickman, M. et al., "Purification and Characterization of Proteasomes from *Saccharomyces cerevisiae*" *Current Protocols in Protein Science*, published by John Wiley & Sons, Inc., pp. 21.5.1 through 21.5.17 (2001).
Coux, O. et al., "Structure and Functions of the 20S and 26S Proteasomes," *Ann. Rev. Biochem.*, 65, pp. 801-847 (1996).
Chondrogianni, N. et al., "Proteasome dysfunction in mammalian aging: Steps and factors involved," *Experimental Gerontolgy*, 40, pp. 931-938 (2005).

* cited by examiner

*Primary Examiner* — Karlheinz R Skowronek
*Assistant Examiner* — Lianko Garyu
(74) *Attorney, Agent, or Firm* — Thompson Hine L.L.P.

(57) ABSTRACT

The present invention relates to peptidic compounds of general formula (I):

$$R_1-X_1-Arg-Lys-Gly-X_2-R_2.$$

In addition, the present invention relates to, on the one hand, a cosmetic or pharmaceutical composition comprising at least one peptide of general formula (I), in a cosmetically or pharmaceutically acceptable medium and, on the other hand, its utilization to prevent or treat the cutaneous signs of aging and photo-aging and to protect the skin from aggressions due to UV radiation. Lastly, the invention applies to a cosmetic treatment process intended to prevent and/or combat the cutaneous signs of aging and photo aging.

16 Claims, No Drawings

```
SEQUENCE LISTING

<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 1

Ile Arg Lys Gly
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 2

Leu Arg Lys Gly Met
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 3

Pro Arg Lys Gly Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 4

Val Arg Lys Gly Phe
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (5)..(5)
<223> OTHER INFORMATION: AMIDATION

<400> SEQUENCE: 5

Val Arg Lys Gly Tyr
1               5

<210> SEQ ID NO 6
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (3)..(3)
<223> OTHER INFORMATION: AMIDATION

<400> SEQUENCE: 6

Arg Lys Gly
1

<210> SEQ ID NO 7
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(3)
<223> OTHER INFORMATION: t-butoxycarbonyl; 7-amido-4-methylcoumarin
```

```
<400> SEQUENCE: 7

Leu Arg Arg
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(4)
<223> OTHER INFORMATION: N-succinyl; 7-amido-4-methylcoumarin

<400> SEQUENCE: 8

Leu Leu Val Tyr
1

<210> SEQ ID NO 9
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(3)
<223> OTHER INFORMATION: (benzyloxy)carbonyl; 7-amido-4-methylcoumarin

<400> SEQUENCE: 9

Leu Leu Glu
1
```

PROTEASOME-ACTIVATING ANTI-AGING PEPTIDES AND COMPOSITIONS CONTAINING SAME

The present invention relates to peptidic compounds of general formula $R_1$—$X_1$-Arg-Lys-Gly-$X_2$—$R_2$ as well as their applications in cosmetics and/or pharmaceuticals in order to prevent and/or correct the effects of aging and photoaging of the skin and keratinous appendages, and to protect the skin against aggressions due to UV radiation.

Aging corresponds to all of the physiological and psychological processes that modify the structure and functions of the organism from a certain age.

Two types of aging can be distinguished, first, intrinsic aging and, second, extrinsic aging. Intrinsic aging is due to genetic factors and biochemical modifications that take place during states of fatigue and stress and hormonal changes such as pregnancy, etc. Extrinsic aging is due to environmental factors to which the organism is subjected throughout its life, such as pollution, sunlight, disease, etc. Aging is a slow and progressive process that affects all cells of the organism by different means and is manifested in different ways. For example, at the level of the skin, the appearance of the skin is modified by various types of internal or external aggressions and then wrinkles and fine lines, hyperpigmentation or hypopigmentation blemishes, dryness or even dehydration of the skin, thinning of the epidermis, elastosis, imperfections, age spots, etc., may appear. All of these changes affect not only the skin, but also the keratinous appendages such as the nails and hair. These modifications are due to, among other causes, alteration of the functions of cell renewal and cellular cohesion and to the synthesis of collagen, elastin and other proteins, leading finally to a reduction in the protective barrier quality of the skin and to an esthetically displeasing appearance of the skin. But one of the main processes responsible for aging of the cells is unquestionably the accumulation of damaged proteins in the cells. In fact, proteins are the target of various abnormal post-translational modifications such as oxidation, glycation and conjugation with products from lipid peroxidation, phenomena whose incidence increases strongly with age.

It is known that free radicals play a key role in the aging process and more particularly in the formation of oxidized, damaged proteins (Harman et al. "Aging: a theory based on free radical and radiation chemistry" J. Gerontol., 11, 298-300). The accumulation of damaged proteins thus poses the problem of the effectiveness of proteolytic systems in charge of eliminating these proteins, and particularly that of the proteasomal system involved not only in eliminating altered proteins, particularly by oxidation, but also in the continuous renewal of intracellular proteins.

The ubiquitin-proteasome pathway plays a fundamental role in a very large number of biological processes. In fact, degradation mechanisms of proteins by proteasome are involved in significant cellular mechanisms such as DNA repair, gene expression control, cell cycle progression regulation, neosynthesized protein quality control, apoptosis or immune response (Glickman and Ciechanover, 2002).

The proteasome present in human cells is a very large size multi-proteinic complex present in the cytoplasm and nucleus. The purified forms of proteasome comprise 2 large subunits; on the one hand, a proteolytic core called proteasome 20S and, on the other hand, a 19S regulating complex that is bound to each of the two ends of the proteasome 20S (Coux et al., 1996; Glickman and Coux, 2001). The 20S proteasome is a particle in a hollow cylinder shape, composed of 28 alpha and beta subunits, distributed in 4 heptameric rings. Peptidase activities are present on the inner surface of the cylinder and affect one another allosterically. Three proteolytic activities ("trypsin, chymotrypsin and caspase-like") have been associated with the 20S proteasome and help destroy proteins into inactive peptides with 3 to 20 amino acids. In addition to the 20S proteasome, the 26S proteasome comprises the 19S regulating complex of 0.7 MDa, constituted of approximately 20 subunits. Recent immunopurification studies have shown that other proteins may be combined with 20S proteasome and 19S (for example the 11S regulating complex).

In view of the diversity of cellular processes controlled via protein degradation, it is not surprising to observe that ubiquitin-proteasome pathway alterations are at the origin of, or closely connected to, several genetic diseases and numerous human pathologies such as colorectal cancers, lymphoma, inflammatory syndromes, or neurodegenerative diseases such as Parkinson's disease or Alzheimer's disease.

Works carried out over these last few years have enabled aging to be correlated with proteasome activity. In fact, while with age there is an increase in the accumulation of oxidized proteins, a lowering in the effectiveness of the proteasomal system is observed (Petropoulos et al., J. Gerontol. A. Biol. Sci. 2000, 55A:B220-7). This reduction in proteasomal system effectiveness was due in fact to a reduction in proteasome quantity. These results have been confirmed by those of a study applying to the quantity and activity of proteasome in cells of centenarian individuals versus young individuals (Chondrogianni et al., Exp. Gerontol. 2000; 35:721-8). These studies, as well as many others, demonstrate the link between aging and proteasome activity and it may be thought that induction of proteasome expression in the skin or keratinous appendage cells could have a positive influence on aging, and even delay aging.

From the perspective of preventing or delaying aging, "natural" cosmetic compositions have been proposed: For example, patent FR 2822701 discloses a composition based on an extract of phaeodactylum algae to promote proteasome activity. Or else, patent application FR 2898808 describes the utilization of a composition comprising an extract of microalga and arginine ferrulate, still to activate proteasome. Other compositions comprise chemical compounds capable of modulating proteasome activity to have an antiaging effect. These compositions are described in patent applications WO 2006/105811 or else WO 2005/061530. However, the proposed peptidic compounds present a large size and it is difficult in the field of cosmetics to use them as such. Therefore a need exists, particularly in the cosmetics industry, for novel compounds presenting a smaller size that are effective as proteasome activators.

This is how the Applicant discovered that compounds of formula $R_1$—$X_1$-Arg-Lys-Gly-$X_2$—$R_2$ were capable of activating proteasome and thus may be useful in order to prevent or treat the cutaneous signs of aging as well as aggressions due to UV radiation.

Consequently, a first object of the present invention is a peptidic compound of general formula (I):

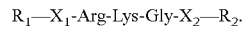

in which, $X_1$ represents an isoleucine, a leucine, a proline, a valine, or is equal to zero, $X_2$ represents a cysteine, a glutamic acid, a glutamine, a histidine, a methionine, a phenylalanine, a tyrosine, a threonine, or is equal to zero, $R_1$ represents the primary amine function of the N-terminal amino acid, free or substituted by a protecting group that may be chosen from among an acetyl group, a benzoyl group, a tosyl group or a benzyloxycarbonyl group, $R_2$ represents the hydroxyl group of the carboxyl function of the C-terminal amino acid, substituted by a protecting group that may be chosen from among an alkyl chain from $C_1$ to $C_{20}$, or an $NH_2$, NHY or NYY group with Y representing an alkyl chain from $C_1$ to $C_4$, said sequence of general formula (I) is constituted of 3 to 5 residues of amino acids, said sequence of general formula (I) may comprise substitutions of amino acids $X_1$ and $X_2$ by other chemically equivalent amino acids.

The second object of the present invention is a cosmetic composition comprising said peptidic compound of formula (I) as an active principle.

In addition, the third object of the present invention is the use of a cosmetic composition comprising said peptidic compound of formula (I) to prevent and/or treat the cutaneous signs of aging and photo-aging and to improve the degradation by proteasome of damaged proteins.

Lastly, the fourth object of the present invention is a method of cosmetic treatment of the skin or keratinous appendages to be treated by using a composition containing said peptidic compound of formula (I).

An object of the present invention is a peptidic compound of the following general formula (I):

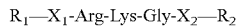

in which, $X_1$ represents an isoleucine, a leucine, a proline, a valine, or is equal to zero, $X_2$ represents a cysteine, a glutamic acid, a glutamine, a histidine, a methionine, a phenylalanine, a tyrosine, a threonine, or is equal to zero, $R_1$ represents the primary amine function of the N-terminal amino acid, free or substituted by a protecting group that may be chosen from among an acetyl group, a benzoyl group, a tosyl group or a benzyloxycarbonyl group, $R_2$ represents the hydroxyl group of the carboxyl function of the C-terminal amino acid, substituted by a protecting group that may be chosen from among an alkyl chain from $C_1$ to $C_{20}$ or an $NH_2$, NHY or NYY group with Y representing an alkyl chain from $C_1$ to $C_4$, said sequence of general formula (I) is constituted of 3 to 5 residues of amino acids, said sequence of general formula (I) may comprise substitutions of amino acids $X_1$ and $X_2$ by other chemically equivalent amino acids.

The peptidic compound according to the invention is characterized in that the compound enables the proteasome activity to be increased.

A peptidic compound that "enables the proteasome activity to be increased" is understood to refer to any biologically active peptide or derivative capable of increasing proteasome activity, either by increasing the protein synthesis of proteasome subunits (by direct or indirect modulation of the gene expression) or by other biological processes such as stabilizing the subunits constituting the proteasome or else stabilizing RNA messenger transcripts.

The peptidic compound according to the invention is characterized in that it activates degradation by proteasome of damaged proteins. "Damaged proteins" is understood to refer to proteins that have undergone oxidation reactions due to reactive species of oxygen (free radicals), glycated or conjugated proteins with products issued from lipid peroxidation, etc.

In a first preferred embodiment, the peptidic compound is protected by an acylation or by an acetylation of the amino-terminal end and/or the carboxy-terminal end.

In a second preferred embodiment, the peptidic compound corresponds to one of the following formulae:

| | |
|---|---|
| Ile-Arg-Lys-Gly-$NH_2$ | (SEQ ID No. 1) |
| Leu-Arg-Lys-Gly-Met-$NH_2$ | (SEQ ID No. 2) |
| Pro-Arg-Lys-Gly-Thr-$NH_2$ | (SEQ ID No. 3) |
| Val-Arg-Lys-Gly-Phe-$NH_2$ | (SEQ ID No. 4) |
| Val-Arg-Lys-Gly-Tyr-$NH_2$ | (SEQ ID No. 5) |
| Arg-Lys-Gly-$NH_2$ | (SEQ ID No. 6) |

Preferentially, the peptidic compound according to the invention corresponds to sequence ID No. 2, i.e., Leu-Arg-Lys-Gly-Met-$NH_2$.

In another preferred embodiment, the peptidic compound according to the invention corresponds to sequence ID No. 6, i.e., Arg-Lys-Gly-$NH_2$.

The invention also relates to homologous forms of these sequences. The term "homologous" designates, according to the invention, any peptide sequence identical to at least 50%, or preferably at least 80%, and still more preferentially to at least 90% of said peptide sequence, chosen from among the SEQ ID No. 1 to SEQ ID No. 6 sequences. "Peptide sequence identical to at least X %" is understood to designate a percentage identity between the amino acid residues of two sequences to be compared, obtained after the optimal alignment of the two sequences. The optimal alignment is obtained by using local homology algorithms such as those used by the BLAST P computer software available on the NCBI site.

The term "homologous" may also designate a peptide that differs from the sequence of a peptide of SEQ ID No. 1 to SEQ ID No. 6 sequence by the substitution of chemically equivalent amino acids, i.e., by the substitution of a residue by another having the same characteristics. Thus, conventional substitutions take place between Ala, Val, Leu and Ile; between Ser and Thr; between the acid residues Asp and Glu; between Asn and Gln; and between the basic residues Lys and Arg; or between the aromatic residues Phe and Tyr.

The amino acids constituting the peptide according to the invention may be in levorotatory, i.e., L- and/or dextrorotatory, i.e., D-configurations; the peptide according to the invention may thus be in L-, D- or DL-form.

The term "peptide" or "peptidic compound" designates a linkage of two or more amino acids interlinked by peptide linkages or by modified peptide linkages.

"Peptide" or "peptidic compound" is understood to refer to the natural or synthetic peptide of the invention as described above, or at least one of its fragments, whether obtained by proteolysis or synthetically, or else any natural or synthetic peptide whose sequence is partially or totally constituted by the sequence of the peptide previously described.

So as to improve resistance to degradation, it may be necessary to use a protected form of the peptide according to the invention. The form of protection must obviously be a biologically compatible form and must be compatible with a use in the field of cosmetics or pharmaceuticals.

Many forms of biologically compatible protection may be contemplated. They are well known to the person skilled in the art such as, for example, acylation or acetylation of the amino ends and/or carboxy-terminal ends. Thus, the invention relates to a composition such as previously defined, characterized by the fact that the peptide of SEQ ID No. 1 to SEQ ID No. 6 is in simple or double protected form. Preferably, protection based on the amidation of the hydroxyl function of the carboxy terminal end by an NYY group with Y representing an alkyl chain from $C_1$ to $C_4$, or the esterification by an alkyl group, is utilized. It is also possible to protect the two ends of the peptide.

The peptide of general formula (I) according to the invention may be obtained either by conventional chemical synthesis (in solid phase or in homogeneous liquid phase), or by enzymatic synthesis (Kullman et al., J. Biol. Chem. 1980, 225, 8234), from constituent amino acids or their derivatives.

The peptide according to the invention may be of natural or synthetic origin. Preferentially according to the invention, the peptide is obtained by chemical synthesis.

Lastly, the active principle may be a single peptide, a mixture of peptides or peptide derivatives and/or constituted of amino acid derivatives.

The peptidic compound according to the invention may be utilized as a medication.

The second object of the present invention relates to a cosmetic composition comprising said peptidic compound of general formula (I) as an active principle. Preferably, the compositions according to the invention are present in a form suitable for topical application comprising a cosmetically acceptable medium. "Cosmetically acceptable" is understood to refer to media that are suitable for a use in contact with the skin or with human keratinous appendages, without risk of toxicity, incompatibility, instability, allergic response or other secondary effects. Preferentially, said peptidic compound is present in the composition at a concentration of between approximately 0.0005 and 500 ppm, and preferentially at a concentration of between 0.01 and 5 ppm. In the compositions according to the invention, the peptidic compound is solubilized in one or more solvents, such as water, glycerol, ethanol, propylene glycol, butylene glycol, dipropylene glycol, ethoxylated diethylene glycol or propoxylated diethylene glycol, cyclic polyols, white petroleum jelly, vegetable oil or any mixture of these solvents.

According to still another advantageous embodiment, the active principle according to the invention is solubilized in a cosmetic or pharmaceutical carrier such as liposomes, or adsorbed on powdery organic polymers, mineral supports such as talcs and bentonites, and more generally solubilized in, or fixed on, any physiologically acceptable carrier.

The compositions intended to be applied on the skin may be present in the form of an aqueous or hydroalcoholic solution, water in oil emulsion or oil in water emulsion, microemulsion, aqueous or anhydrous gel, serum, or else vesicle dispersion, patch, cream, spray, ointment, pomade, lotions, colloid, solution, suspension or other forms. The compositions may also be applied onto the keratinous appendages in the form of shampoo, hair tint or mascara to be applied by brush or comb, in particular onto the eyelashes, eyebrows or hair, or else nail treatment such as nail polish.

In a particular embodiment, the composition according to the invention also contains at least one other active principle promoting the action of said peptidic compound. In a non-limiting manner, the following classes of ingredients may be cited: Other peptide active agents, vegetable extracts, cicatrizant, anti-age, anti-wrinkle, soothing, anti-radical, anti-UV agents, agents stimulating the synthesis of dermic macromolecules or energy metabolism, moisturizing, antibacterial, antifungal, anti-inflammatory, anesthetic agents, agents modulating cutaneous differentiation, pigmentation or depigmentation, agents stimulating nail or hair growth. Preferentially, an agent presenting activity in the field of anti-wrinkles will be utilized, such as an anti-radical or antioxidant agent, or an agent stimulating the synthesis of dermic macromolecules or else an agent stimulating energy metabolism. More particularly, the active principle is chosen from among vitamins, phytosterols, flavonoids, DHEA and/or one of its precursors or one of its chemical or biological derivatives, a metalloproteinase inhibitor or a retinoid. In addition, additives such as thickening agents, emulsifiers, humectants, emollients, fragrances, antioxidants, film-forming agents, chelating agents, sequestering agents, conditioners, etc., may be added to the composition.

In all cases, the person skilled in the art will make sure that these adjuvants as well as their proportions are chosen so as to not harm the desired advantageous properties of the composition according to the invention. These adjuvants may, for example, range between 0.01 to 20% of the total weight of the composition. When the composition of the invention is an emulsion, the fatty phase may represent from 5 to 80% by weight and preferably from 5 to 50% by weight with relation to the total weight of the composition. The emulsifiers and co-emulsifiers utilized in the composition will be chosen from among those conventionally utilized in the field under consideration. For example, they may be utilized in a proportion going from 0.3 to 30% by weight with relation to the total weight of the composition.

Lastly, the invention relates to a composition comprising said peptidic compound in order to increase proteasome activity and improve degradation by proteasome of damaged proteins.

A third object of the invention relates to the utilization of a cosmetic composition comprising said peptidic compound and a cosmetically acceptable medium to prevent and/or treat the cutaneous signs of aging and photo-aging.

"Cutaneous signs of aging" include, but are not limited to, all manifestations visible on the skin caused by aging. In particular, this is understood to refer to wrinkles, deep and coarse wrinkles, fine lines, scratches, sagging cutaneous and subcutaneous tissues, the loss of skin elasticity and atonia, the loss of firmness and tonicity, and skin atrophy. In addition, "cutaneous signs of aging" is also understood to refer to enlarged pores, imperfections, discoloration, age spots, keratosis, loss of collagen and other changes in the dermis and epidermis, but also any modifications in the external appearance of the skin and keratinous appendages due to aging such as, for example, superficial roughness of the horny layer of epidermis, but also any internal modification of the skin that does not systematically result in a modified external appearance such as, for example, thinning of the dermis. "Photo-aging" is understood to refer to the premature aging of the skin caused by prolonged and cumulative sun exposure.

The present invention thus relates to the utilization of a composition to treat or prevent wrinkles, deep and coarse wrinkles, fine lines, scratches, sagging cutaneous and subcutaneous tissues, the loss of skin elasticity and atonia, the loss of firmness and tonicity and skin atrophy. In addition, said composition according to the invention activates cell renewal and thoroughly cleans the cells.

Another object of the invention relates to the utilization of a composition according to the invention to protect the skin against aggressions due to UV radiation. Lastly, the invention relates to the utilization of a composition comprising the peptidic compound to increase proteasome activity and improve degradation by proteasome of damaged proteins.

A final object of the present invention relates to a cosmetic treatment method characterized in that a composition comprising an effective quantity of peptidic compound according to the invention is applied topically to the skin or keratinous appendages to be treated to prevent and/or treat the cutaneous signs of aging and photo-aging. In addition, this cosmetic treatment method is characterized in that the composition is applied before bedtime so as to clean the cells and skin during the cell renewal cycle. In fact, during the night, the skin prioritizes renewal functions as well as metabolic synthesis processes. Consequently, the application of the composition as claimed, by respecting the biological rhythm of the skin, enables a rejuvenating, stimulating cell renewal, and regenerating effect to be obtained.

The following examples describe and demonstrate the effectiveness of peptidic compounds as described according to the invention but should not be interpreted as a limitation of the present invention.

EXAMPLE 1

Validation of the Aged Keratinocyte Model: Immunoblotting of Ubiquitinylated Proteins and 20S Proteasome on Aged Keratinocytes Aging Process of Keratinocytes in Culture Normal Human Keratinocytes (NHK), cells are isolated from human skin biopsies. These cells are maintained in culture in a special keratinocyte-SFM medium (Invitrogen) at 37° C. under a humidified atmosphere of 5% $CO_2$. Aged NHK cells are obtained by performing a series of repeated subcultures. Briefly the cells are seeded in 75 $cm^2$ flasks, at low density and cultured from 5 to 10 days between 2 passages. The cells are treated or not treated by the active principle, by adding the active principle directly into the culture medium 3 times per week. The cells are then maintained under these conditions for 45 days.

Immunoblotting of Ubiquitinylated Proteins and 20S Proteasome on Aged Keratinocytes In order to validate our model, it should first of all be demonstrated that on experimentally aged keratinocytes in culture, the level of ubiquitinylated protein expression, as well as the level of 20S proteasome, in accordance with the literature, reduced over time. The level of expression of these proteins was evaluated by the immunoblotting technique. The immunoblotting (or western blotting) technique is a semi-quantitative method that enables the level of proteins studied in cells, i.e., the level of proteins ubiquitinylated by a ubiquitin specific antibody (DAKO), as well as the level of 20S proteasome by a proteasome specific antibody (CALBIOCHEM), to be determined.

Protocol:

Aged keratinocytes are cultured in 75 $cm^2$ flasks at 37° C. in a humidified atmosphere containing 5% of $CO_2$ for 10, 20, 30 and 40 days. The cells are not treated on the day of the experiment. The cells are rinsed and then detached from the support by using an extraction buffer (20 mM TRIS, 150 mM NaCl, 10 mM EDTA, 0.2% Triton X10) in the presence of a protease inhibitor cocktail (Sigma). The proteins thus extracted are centrifuged at 4° C. at 10000 rpm for 10 minutes before being assayed by the BCA protein assay kit (Pierce). The cellular lysates are mixed with a denaturing buffer and subjected to SDS PAGE electrophoresis. The gel used is a Nupage 4-12% gel (Invitrogen). The proteins are then transferred to a nitrocellulose membrane (Pal corporation). The membranes are saturated in PBS-milk 5%, 0.1% Tween 20, 2 hours at ambient temperature, and then incubated at 4° C. throughout the night with a primary antibody.

For the ubiquitinylated protein study, the primary antibody is a rabbit anti-ubiquitin antibody utilized at the 1/500th dilution (DAKO).

For the 20S proteasome study, the primary antibody is a mouse anti-20S proteasome antibody utilized at the 1/1000th dilution (CALBIOCHEM).

The incubation with the primary antibody is followed by incubation with an anti-rabbit IgG-peroxidase secondary antibody (IMMUNOTECH) diluted to 1/1000th in the case of ubiquitinylated proteins, or with an anti-mouse IgG-peroxidase secondary antibody (IMMUNOTECH) diluted to 1/1000th in the case of proteasome. The development is carried out by a chemiluminescent substrate. Evaluation of proteins expressed in the cells is carried out by the Chemiimager software (Alpha Innotech Corporation USA). The quantity of proteins studied is expressed as a percentage of the luminous intensity compared to the control condition at time 0 of the experiment.

Results:

Immunoblotting of Ubiquitinylated Proteins on Keratinocytes During Aging:

| Intensity (%) | Experiment 1 |
| --- | --- |
| Untreated 10 days | 100% |
| Untreated 20 days | 71% |
| Untreated 30 days | 64% |
| Untreated 50 days | 56% |

Immunoblotting of 20S Proteasome on Keratinocytes During Aging

| Intensity (%) | Experiment 1 |
| --- | --- |
| Untreated 10 days | 100% |
| Untreated 20 days | 94% |
| Untreated 30 days | 47% |
| Untreated 50 days | 54% |

Conclusion:

We have thus demonstrated, in our experimental aging system, that the level of ubiquitinylated proteins reduces over time and, proportionally to the culture time, after 40 days we registered a reduction of approximately 56% with relation to time 0. In the same manner we have demonstrated, in our experimental aging system, that the level of 20S proteasome reduces over time and, proportionally to the culture time, after 40 days we registered a reduction of approximately 54% with relation to time 0.

These 2 experiments allowed us to conclude that the experimental aging put in place in the laboratory is a good study model of aging on cells in culture. This model may thus be utilized in subsequent experiments to demonstrate the activity and effectiveness of our active principle.

EXAMPLE 2

Demonstration of the Activator Effect of the Active Principle on Measuring the Enzymatic Activity of 20S Proteasome on Aged Keratinocytes Maintained in Culture Experimentally aged keratinocytes maintained in culture for 15 days are treated with 1% of peptide SEQ ID No. 6. The enzymatic activities of 20S proteasome are then studied. In fact, 20S proteasome is the subunit responsible for enzymatic hydrolysis. Three enzymatic activities may be studied: Trypsin-like, chymotrypsin-like and peptidylglutamyl-peptide hydrolase (PGPH) activity. We are proposing to study these activities by a specific enzymatic assay of each activity.

Protocol:

The aged keratinocytes are maintained in culture for 15 days. The cell treatment is carried out by adding a solution at 1% of peptide SEQ ID No. 6 directly into the medium, renewed 3 times per week for the time of the experiment. The assay of each activity was carried out by using specific substrates labeled by a fluorescent compound 7-amido-4-methylcoumarin (AMC). After cleavage, the AMC excitation wavelength is 350 nm, the fluorescence is read at 440 nm. The fluorescence intensity is proportional to the quantity of fluorochrome obtained and consequently, this quantity is proportional to the quantity of hydrolyzed substrate.

The synthetic peptide Boc-Leu-Arg-Arg-AMC is specific for trypsin activity.

The synthetic peptide Suc-Leu-Leu-Val-Tyr-AMC (SEQ ID NO: 8) is specific for chymotrypsin activity.

The synthetic peptide Z-Leu-Leu-Glu-AMC is specific for peptidylglutamyl-peptide hydrolase activity.

These peptides have been provided and labeled by SIGMA ALDRICH, Saint-Louis, Mich., USA.

The cells are detached from the support in an extraction buffer. Afterwards, the cells are sonicated for 1 minute at 4° C., and then centrifuged at 15000 g for 30 minutes at 4° C. The protein assay is carried out by the BCA kit (Pierce). After incubation of the cellular lysate with the synthetic substrate specific for the activity studied, fluorescence is read with the Synergy spectrophotometer (BIOTEK, Vermont, USA) at 440 nm.

Results:

We observe that for the 3 activities studied, peptide SEQ ID No. 6 enabled the enzymatic activity of 20S proteasome to be increased. The trypsin-like activity is increased by 155.3% during treatment by the active principle, the chymotrypsin-like activity is increased by 130% and an increase of 144.6% is recorded for the peptidylglutamyl-peptide hydrolase activity.

Conclusions:

Peptide SEQ ID No. 6 utilized at 1% on keratinocytes aged experimentally in culture enable the specific enzymatic activities of 20S proteasome to be increased.

The experiment was performed several times, and a statistical test (t-Student statistical test) could have been carried out. The increase in activities is significant for the study of trypsin-like, chymotrypsin-like activity ($p=0.033$ and $p=0.0477$ respectively), and highly significant for peptidyl-glutamyl-peptide hydrolase activity ($p=0.00053$).

EXAMPLE 3

Demonstration of the Activator Effect of the Active Principle on the Proliferation of Aged Keratinocytes in Culture A study of the activator effect of peptide SEQ ID No. 2 was carried out by evaluating the expression of the cellular proliferation marker protein on experimentally aged keratinocytes in culture. The analysis is carried out after 20 days of culture.

Immunoassay:

In vitro studies of keratinocytes aged experimentally in culture for 20 days have demonstrated, by immunolabelling, the expression of the Ki67 protein, which is a proliferation marker. The keratinocytes are cultured for 20 days in a $CO_2$ incubator at 37° C. under humidified atmosphere. The cells are treated directly by adding 1% peptide directly into the medium. Cells that are not treated but aged in the same manner are used as control cells. For experimental requirements, the cells are seeded in 8-well labteck, maintained in culture and treated in the same support until the day of labeling. On the day of immunolabelling, the cells are rinsed by using phosphate buffer and then fixed with cold methanol before labeling.

Immunolabelling is carried out by a rabbit anti-Ki67 antibody (Abcam) diluted to $1/1000^{th}$ and a secondary antibody to $1/1000^{th}$ coupled with an Alexa fluor monkey anti-rabbit fluorochrome (Molecular probes).

The slides are then mounted in a suitable medium and observed by epifluorescence microscope (Nikon Eclipse E E600).

Results/Conclusions:

The results obtained show that the intensity of labeled cells under control conditions is lower than under conditions treated by the active principle.

The active principle increased the Ki67 protein in aged and treated cells compared to untreated cells. The Ki67 proliferation marker enabled a proliferation of aged keratinocytes to be demonstrated when they are treated by the active principle.

EXAMPLE 4

Demonstration of the Antiaging Effect of the Active Principle on Aged Keratinocytes in Culture A study of the antiaging effect of the active principle was carried out by evaluating the expression of the beta-galactosidase protein on experimentally aged keratinocytes in culture. In fact, labeling of beta-galactosidase is known to be present in senescent cells while galactosidase activity is not found in pre-senescent, quiescent or immortal cells.

Protocol:

Keratinocytes experimentally aged in 8-well labteck are cultured and maintained for 20 days in the presence or not of 1% peptide of SEQ ID No. 6. The treatment is carried out 3 times per week by direct addition into the medium.

Untreated cells are maintained in culture for the same experiment time and will be used as controls. On the day of labeling, the cells are rinsed and fixed in a 2% glutaraldehyde-2% formaldehyde mixture for 3 minutes. The cells are then rinsed and 300 µl of 5-bromo-4-chloro-3 indolyl b-D-galactosidase, commonly called X-gal (substrate of beta-galactosidase), is applied. Incubation is carried out for 24 hours in the $CO_2$ incubator, and then the cells are rinsed and the labteck is quickly mounted in a suitable medium. Observation is carried out by transmission microscope. The principle is simple: When the cells are senescent and contain beta-galactosidase, the X-gal substrate is cleaved into a blue insoluble product. Beta-galactosidase activity is demonstrated by coloration of blue cells. The more blue cells, the higher the number of senescent cells.

Results/Conclusions:

We observe that in the presence of active principle, beta-galactosidase activity is strongly reduced in the treated cells compared to the untreated cells.

Consequently, the active principle demonstrates an antiaging effect on keratinocytes in culture experimentally aged for 20 days of culture.

EXAMPLE 5

Evaluation of Protein Carbonylation of Fibroblasts Treated by the Active Principle and Subjected to Ultraviolet Radiation (UVB)

Protocol:

Normal human fibroblasts in culture are seeded in containers of 100 diameter. When the cells have reached 70% confluency, the cells are treated for 48 hours with the peptide of sequence ID No. 6 diluted to 1% in the medium. The cells are subjected to UVB irradiation at 100 mj/cm$^2$, and then returned 48 additional hours in the presence of the active principle. Control containers with cells untreated by the active principle but irradiated are used as controls. The cells are rinsed and then detached from the support by using a suitable extraction buffer. The proteins thus extracted are centrifuged at 4° C. at 10000 rpm for 10 minutes before being assayed by the BCA protein assay kit (Pierce). Protein carbonylation is carried out by a test based on the immunodetection of carbonyl groups previously derived by 2,4-dinitrophenylhydrazine (DNP) (SIGMA).

According to the reaction:

Protein —C=O+H2N—NH-2.4DNP→Protein —C=N—NH2.4-DNP+H2O

Briefly, 15 µl of the sample is caused to react with 45 µl of DNP for 45 minutes at ambient temperature. Then, 5 µl of the mixture is diluted in 1 ml of phosphate buffer saline and 200 µl of this dilution is put in a 96-well plate overnight at 4° C. in the presence of 150 µl of BSA (fraction V).

After 3 washings in phosphate buffer saline (PBS), the rabbit anti-dinitrophenyl biotinylated antibody (CALBIOCHEM) is diluted to 1/5000th in 0.1% serum albumin buffer in the presence of 0.1% Tween 20 and incubated in microplates 1 hour at 37° C. After 3 washings, the streptavidin-peroxidase complex (DAKO) diluted to 1/3000th is incubated in 0.1% serum albumin buffer in the presence of 0.1% Tween 20 and incubated in microplates for 1 hour at ambient temperature. After 3 washings, the development is carried out thanks to 200 µl of tetramethylbenzidine (TMB, SIGMA) 25 minutes at ambient temperature. Then, 100 µl of sulfuric acid at 2.5 M is added to stop the reaction. The OD is read at 490 nm. In order to convert the OD obtained into carbonyl groups present in the samples, a calibration curve was established by varying the proportions from 0 to 100% of oxidized BSA.

Results:

In the presence of UVB, the untreated cells are strongly carbonylated and increase by 110% with relation to the non-irradiated and untreated cells. In the presence of the active principle at 1%, the carbonylation level is reduced by 34%. The experiment was performed several times, and a statistical test (t-Student statistical test) could have been carried out. The carbonylation reduction is significant and p=0.0298.

In conclusion, the active principle enables the cells to be protected from the harmful effects of UV radiation, i.e., from its oxidative effects. The active principle enables protein oxidation to be reduced by more than 34%.

Applicants incorporate by reference the material contained in the accompanying computer readable Sequence Listing entitled "ISP12_textSEQ.txt", which was created on Dec. 26, 2013, and is 2,347 bytes in size, and hereby confirm that the information recorded in the computer readable form is identical to the written sequence listing.

The invention claimed is:

1. A cosmetic composition comprising:
a peptidic compound in a cosmetically acceptable medium for topical application, the peptide compound having the following general formula (I):

$R_1$—$X_1$-Arg-Lys-Gly-$X_2$—$R_2$ in which,
$X_1$ represents an isoleucine, a leucine, a proline, or a valine,
$X_2$ represents a cysteine, a glutamic acid, a glutamine, a histidine, a phenylalanine, a tyrosine, a threonine, or is equal to zero,
$R_1$ represents the primary amine function of the N-terminal amino acid, free or substituted by a protecting group, wherein the protecting group is an acetyl group, a benzoyl group, a tosyl group or a benzyloxycarbonyl group,
$R_2$ represents the hydroxyl group of the carboxyl function of the C-terminal amino acid, substituted by a protecting group, wherein the protecting group is an alkyl chain from $C_1$ to $C_{20}$, or an $NH_2$, NHY or NYY group with Y representing an alkyl chain from $C_1$ to $C_4$, said sequence of general formula (I) is constituted of 4 to 5 residues of amino acids.

2. The cosmetic composition according to claim 1, wherein said peptidic compound is present in the composition at a concentration of between approximately 0.0005 and 500 ppm.

3. The cosmetic composition according to claim 1, wherein said peptidic compound is solubilized in one or more solvents selected from the group consisting of water, glycerol, ethanol, propylene glycol, butylene glycol, dipropylene glycol, ethoxylated or propoxylated diethylene glycols, cyclic polyols, white petroleum jelly, vegetable oil, and combinations thereof.

4. The cosmetic composition according to claim 1, further comprising at least one active principle promoting the action of said peptidic compound.

5. The cosmetic composition according to claim 4, wherein said active principle is selected from the group consisting of vitamins, phytosterols, flavonoids, dehydroepiandrosterone (DHEA), DHEA precursors, DHEA chemical or biological derivatives, a metalloproteinase inhibitor, and a retinoid.

6. The cosmetic composition of claim 1, wherein said peptidic compound is present in the composition at a concentration of between 0.01 and 5 parts per million (ppm).

7. The composition of claim 1, wherein the peptidic compound is one of the following sequences:

Ile-Arg-Lys-Gly-NH$_2$;   (SEQ ID NO: 1)

Pro-Arg-Lys-Gly-Thr-NH$_2$;   (SEQ ID NO: 3)

Val-Arg-Lys-Gly-Phe-NH$_2$; or   (SEQ ID NO: 4)

Val-Arg-Lys-Gly-Tyr-NH$_2$.   (SEQ ID NO: 5)

8. A cosmetic composition comprising a peptidic compound consisting of SEQ ID NO: 2 in a cosmetically acceptable medium for topical application.

9. A cosmetic composition comprising a peptidic compound consisting of SEQ ID NO: 6 in a cosmetically acceptable medium for topical application wherein said composition protects the skin from aggressions due to ultraviolet (UV) radiation.

10. A method of protecting or treating the cutaneous signs of aging and photo-aging in skin or keratinous appendages, the method comprising:
   providing an effective quantity of the cosmetic composition of claim 1 or claim 8 or claim 9; and
   topically applying the composition to the skin or keratinous appendages to be treated.

11. The method of claim 10, wherein signs of aging include one or more of wrinkles, deep and coarse wrinkles, fine lines, scratches, sagging cutaneous and subcutaneous tissues, the loss of skin elasticity and atonia, the loss of firmness and tonicity, and skin atrophy.

12. The method of claim 10, wherein said composition activates cell renewal and thoroughly cleans the cells.

13. The method of claim 10, wherein said composition is the cosmetic composition of claim 1 or claim 8, said composition protects the skin from aggressions due to ultraviolet (UV) radiation.

14. The method of claim 10, wherein the cosmetic composition increases proteasome activity and improves degradation by proteasome of damaged proteins.

15. The method of claim 10, wherein the cosmetic composition is applied before bedtime so as to clean the skin during cell renewal cycle.

16. The method of claim 10, wherein the peptidic compound is one of the following sequences:

```
                                          (SEQ ID NO: 1)
    Ile-Arg-Lys-Gly-NH2;

(SEQ ID NO: 3)
    Pro-Arg-Lys-Gly-Thr-NH2;

(SEQ ID NO: 4)
    Val-Arg-Lys-Gly-Phe-NH2; or (SEQ ID NO: 5)
    Val-Arg-Lys-Gly-Tyr-NH2.
```

\* \* \* \* \*